United States Patent [19]

Bolton et al.

[11] Patent Number: 4,945,904

[45] Date of Patent: Aug. 7, 1990

[54] ORTHOPEDIC DRILL GUIDE DEVICE

[75] Inventors: Carl W. Bolton, Flagstaff, Ariz.; Robert R. Oden, Aspen, Colo.; Stanislaw L. Zukowski, Flagstaff, Ariz.

[73] Assignee: W. L. Gore & Associates, Inc., Newark, Del.

[21] Appl. No.: 427,164

[22] Filed: Oct. 25, 1989

[51] Int. Cl.$^5$ ............................................. A61F 2/00
[52] U.S. Cl. ......................................................... 606/96
[58] Field of Search ...................... 606/79, 87, 88, 96, 606/97, 98, 104, 53, 102

[56] References Cited

U.S. PATENT DOCUMENTS 4,535,768  8/1985  Hourahane ........................ 606/96
4,672,957  6/1987  Hourahane ........................ 606/96
4,708,139 11/1987  Dunbar, IV ....................... 606/96
4,781,182 11/1988  Purnell ............................. 606/96

OTHER PUBLICATIONS

Magnus Odensten, M.D., Ph.D., "Treatment of the Torn Anterior Cruciate Ligament", Linkoping University Medical Dissertations No. 177, pp. 28-30, Linkoping, Sweden.

Robert C. Hendler, M.D., "A Unitunnel Technique for Arthroscopic Anterior Cruciate Ligament Reconstruction", Techniques in Orthopaedisc, 1988, 2(4):52-59.

Primary Examiner—Mickey Yu
Assistant Examiner—Michael Brown
Attorney, Agent, or Firm—Gary A. Samuels

[57] ABSTRACT

An orthopedic drill guide device is described, its intended use being to locate and guide the drilling of holes in bone for the purpose of implanting tissue repair devices.

23 Claims, 2 Drawing Sheets

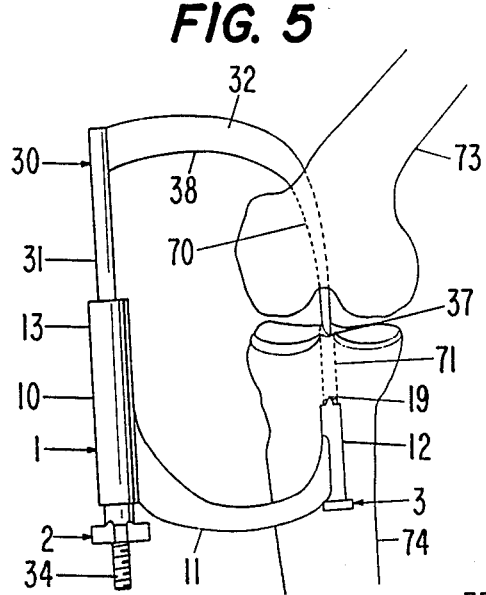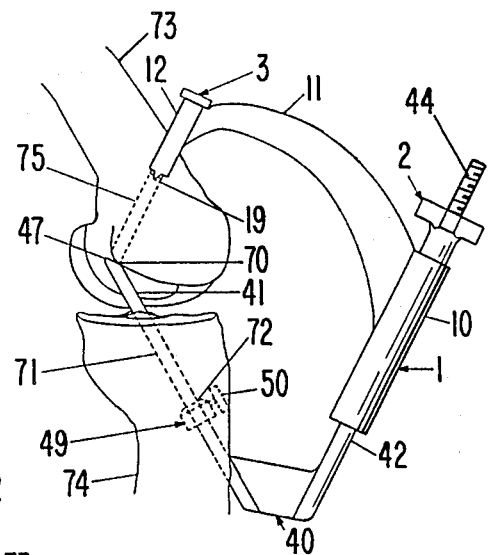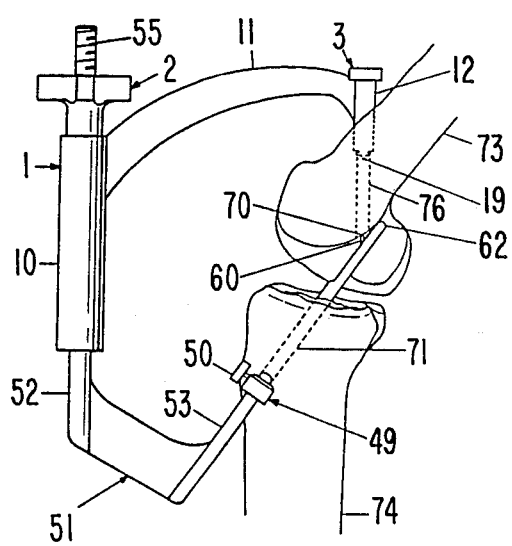

ORTHOPEDIC DRILL GUIDE DEVICE

FIELD OF THE INVENTION

This invention relates to an orthopedic drill guide device.

BACKGROUND OF THE INVENTION

Tissue repair materials for the repair or replacement of connective tissue have existed for some time. These materials can be synthetic or biological materials or combinations thereof. The most common of these are ligament augmentation devices and ligament replacement devices for the repair or replacement of damaged cruciate ligaments. These devices are typically implanted by drilling a through-hole into the proximal end of the tibia and another through-hole into the distal end of the femur. The tissue repair device is pulled through these two holes, the two ends of the device extending some length beyond the extreme ends of the through-holes and secured to adjacent bone, typically with bone screws, staples, sutures or combinations thereof.

In the case of the repair or replacement of the anterior cruciate ligament, the through-hole in the proximal end of the tibia is typically drilled from below, the drill entering the anteromedial side of the tibia and emerging at the anatomic attachment site on the tibial plateau. The corresponding through-hole in the distal end of the femur is typically drilled in one of two locations, chosen according to the intended placement of the ligament repair device. "Anatomic placement" of the device requires a through-hole drilled from the lateral femoral epicondylar area and emerging at the origin of the anterior cruciate ligament on the posteromedial aspect of the lateral femoral condyle. The alternative placement of the tissue repair device is called "over-the-top" placement which may or may not necessitate a femoral through-hole. In the case requiring a femoral through-hole, the through-hole begins at a point four or five centimeters proximal to the lateral femoral epicondyle on the lateral shaft of the femur. The through-hole is directed posterior, medial and inferior to exit at a point just proximal to the capsular attachment and lateral to the midline of the axis of the femur.

In recent years it has become apparent that a high degree of precision is required to assure proper placement of the drilled through-holes if tissue repair materials are to function properly and reliably. As both the entry and exit site of each through-hole are subject to error due to the relatively poor access and difficulty in recognizing correct orientation during this type of surgery, several different types of drill guides have been designed to reduce the likelihood of error.

These drill guides may be divided into two categories, the first being guides that drill the tibial and femoral through-holes independently with the result that the relative locations of the two holes with respect to each other are not assured. Most commercially available drill guides at present are designed to function in this manner. By failing to provide for the proper relationship between the two holes, the use of these drill guides often results in an abrupt angle between the segment of the tissue repair device located between the drilled through-holes, called the intra-articular segment, and the portions of the device located within the through-holes. This abrupt angulation can result in premature wear and failure of the tissue repair material as the material works in tension over the edges of the drilled through-holes.

In addition, these types of drill guides suffer from various combinations of the following problems: (1) inadequate rigidity, (2) moveable joints allowing excessive flexibility, (3) locating probes subject to inaccurate placement, (4) inability to provide for both anatomical and over-the-top ligament placement, (5) insecure attachment of the drill guide to the bone surface resulting from lack of gripping features on the appropriate drill guide surface, inadequate securing force or securing force applied other than axially to the drill guide, and (6) axial orientation of locating probe tip and drill guide without a planar third point reference to the desired bone surfaces.

The second type of drill guide makes an attempt to align the femoral and tibial through-holes. At this time only a few such devices are available. With these drill guide systems, a single drilling is performed to create both the tibial and femoral through-holes on the same axis. One of these devices consists of two extra-articular and one intra-articular guide posts attached to a common cross-bar. The drill pilot, attached to the end of an extraarticular guide post opposite the end slideably attached to the cross bar, is axially secured without teeth using a screw to provide secure location. Because it locates primarily from its intra-articular guide post in a pivotal fashion and because both extra-articular guide posts are slideably mounted, the drilled through-holes may be correctly centered by the intra-articular guide post but angularly mis-located by improper location of the extra-articular guide posts on the cross-bar.

Another such device that relies on the concept of tibial and femoral through-holes drilled on the same axis uses a guide that clamps between the surfaces of the tibial plateau and the anterior face of the femur. In use with this device the knee is bent to an angle of about ninety degrees. This drill guide is subject to inaccurate placement and does not provide for a secure attachment to the tibia.

There are several fundamental problems with present drill guides designed to drill tibial and femoral through-holes on a common axis. They only provide ideal alignment of the tissue repair device when the knee is highly flexed, at which position it is typically under lower load. When the leg is straightened and highly loaded the tissue repair device is most severely angulated. These devices can also cause misalignment between the two holes because the femur and tibia, connected by a damaged or broken anterior cruciate ligament, are subject to lateral displacement relative to each other during drilling. Additionally, these drill guides are only capable of anatomical placement of a tissue repair device and cannot provide for over-the-top placement.

SUMMARY OF THE INVENTION

The drill guide device of the present invention overcomes deficiencies of previously available drill guide systems. It is designed to accurately locate, align and guide the drilling of the tibial through-hole and then to locate, align and guide the drilling of the femoral through-hole with respect to the previously drilled tibial through-hole. In use it provides means to locate the tibia with respect to the femur regardless of damage to the secondary restraints of the knee, i.e. lateral ligaments and capsular tissue, during placement and drilling of the femoral through-hole. The drill guide of this invention incorporates five main components: a handle, a tibial component, a femoral component for over-the-top placement, another femoral component for anatomical placement, and a threaded nut.

The handle is used in conjunction with the tibial component and the threaded nut to locate, align and guide the drilling of the tibial through-hole. The handle and threaded nut are then used with either femoral component to locate, align and guide the drilling of the femoral through-hole in relation to the previously drilled tibial through-hole.

The handle is secured to the appropriate femoral or tibial component by tightening the nut on the threads of the component. Tightening this nut compressively secures the drill guide device to the correct drill entry site with a bone engaging tooth of the pilot tube.

BRIEF DESCRIPTION OF THE DRAWINGS

FIG. 5 depicts the drill guide device in use with the tibial component, correctly located, aligned and secured to the tibia for drilling of the tibial through-hole.

FIG. 6 depicts the drill guide device in use with the femoral component, correctly located, aligned and secured to the femur for drilling of the femoral through-hole appropriate for over-the-top placement of a tissue repair device.

FIG. 7 depicts the drill guide device in use with the femoral component, correctly located, aligned and secured to the femur for drilling of the femoral through-hole appropriate for anatomic placement of a tissue repair device.

DETAILED DESCRIPTION OF THE INVENTION

Figure 1:
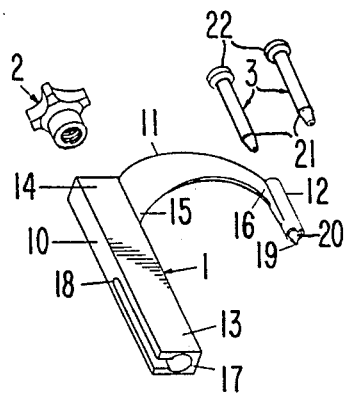
FIG. 1 depicts the handle, threaded nut, and alternative hollow bullet-shaped pilots.
Figure 2:
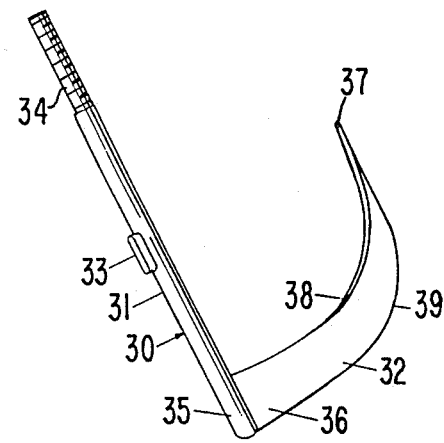
FIG. 2 depicts the tibial component.
Figure 3:
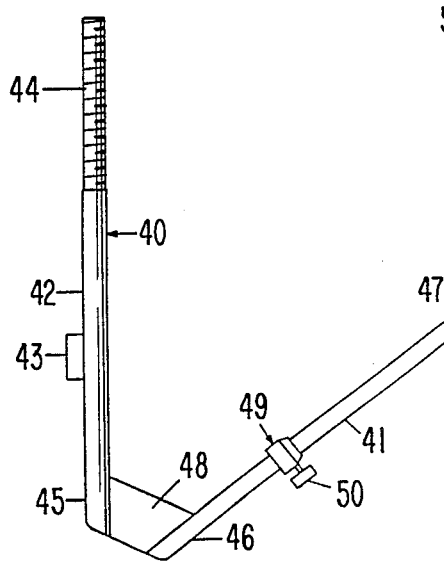
FIG. 3 depicts the femoral component for use when placing a tissue repair device in over-the-top position.
Figure 4:
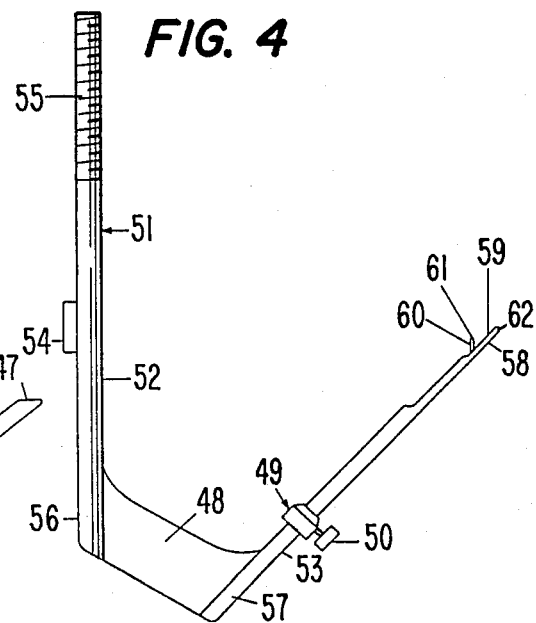
FIG. 4 depicts the femoral component for use when placing a tissue repair device in anatomic position.

As configured for drilling a tibial through-hole, the drill guide device comprises a handle and a threaded nut (FIG. 1) and a tibial component (FIG. 2). For drilling a femoral through-hole, the drill guide device comprises a handle and a threaded nut (FIG. 1) and a femoral component. The femoral component is of two types depending on the desired placement of the tissue repair device: the femoral component for over-the-top placement (FIG. 3) and the femoral component for anatomic placement (FIG. 4).

As shown by FIG. 1, the handle (1) is comprised of an arm (11), a hollow sleeve (10) and a pilot tube (12), each of which has a first and second end. The second end (14) of the hollow sleeve (10) is attached to the first end (15) of the arm (11). The hollow sleeve (10) is of constant inside diameter (17) for its full length, this diameter being intended to accommodate the outside diameter of the alignment rod of either the tibial (FIG. 2) or femoral (FIG. 3 or 4) component. A slot (18) is cut through the wall of the hollow sleeve (10) and extends longitudinally for all or some part of the length of the hollow sleeve (10) beginning from the first end (13) of the hollow sleeve (10). The slot (18) is preferably centered over the longitudinal axis of the hollow sleeve (10).

The pilot tube (12) is attached to the second end (16) of the arm (11). The axis of the pilot tube (12) is parallel to the axis of the hollow sleeve (10). There are one or more bone-engaging teeth (19) affixed to the end of the pilot tube (12) closest to the tibial component locating arm (FIG. 2) or femoral component locating rod (FIG. 3 or 4) when either component is properly fitted to the handle (FIG. 1). Preferably there are two such teeth (19), the points of which are located on opposite sides of one end of the pilot tube (12).

The inside diameter (20) of the pilot tube (12) is of a diameter such that it will accurately accommodate the desired drill size. Alternatively and preferably the inside diameter (20) of the pilot tube (12) is intended to accommodate a removable hollow bullet-shaped pilot (3). This removable hollow bullet-shaped pilot (3) will have a constant inside diameter to accurately accommodate a particular drill size. As this hollow bullet-shaped pilot can be removed from the pilot tube (12) of the handle (1), it is seen that hollow bullet-shaped pilots (3) of a range of various inside diameters may be used with the same handle (1). It is therefore possible to use the same drill guide assembly with a first smaller pilot drill and a second larger final drill. Alternatively, a K-wire may be used rather than a smaller pilot drill.

Hollow bullet-shaped pilots (3) may be removably retained within the pilot tube (12) during use by a retaining ring (21) or by any other suitable means. The removable hollow bullet-shaped pilot (3) may incorporate a knurled knob (22) at one end to facilitate insertion and removal. Means may be provided for slideably aligning the hollow bullet-shaped pilot (3) with the pilot tube (12) so that the hollow bullet-shaped pilot (3) is prevented from turning with the drill during drilling.

The threaded nut (2) is intended to secure either the tibial component (FIG. 2) or the femoral component (FIG. 3 or 4) to the handle (1) and to secure the assembly to the femur and tibia. The threaded nut (2) may be a separate part or may be rotatably attached to the handle (1).

As shown by FIG. 2, the tibial component (30) used with the handle (1) and threaded nut (2) allows accurate and positive location and drilling of the tibial through-hole. The tibial component (30) comprises an alignment rod (31), a locating arm (32) and an alignment key (33). These are all integral parts not intended to be removable from each other.

The alignment rod (31) has a first (34) and second (35) end. It is threaded beginning from the first end (34) and extending for all or a part of the length of the alignment rod (31). The second end (35) of the alignment rod (31) is attached to the first end (36) of the locating arm (32), said locating arm (32) also having a second end (37) which is tapered to a sharp point (37). The preferred method of attaching the locating arm (32) to the alignment rod (31) is welding. Any method may be used that provides a rigid attachment. The locating arm (32) is preferably of curved form, having inner (38) and outer (39) curved edges and a shape somewhat like the blade of a sickle. The curvature is of approximately constant radius extending through an arc of about 90 degrees. Both the inner (38) and outer (39) curved edges extend from the pointed second end (37) of the locating arm (32), the outer curved edge (39) being of larger radius than the inner curved edge (38) so that at the intersection with the alignment rod (31), the curves are far enough apart to allow an adequate width for rigid attachment of the first end of locating arm (36) to the second end of the alignment rod (35). Other shapes may be used for the locating arm (32) so long as they allow for rigid attachment to the alignment rod (31), have a pointed end (37), and so contact the femur that the desired alignment is provided.

The final part of the tibial component (30) is the alignment key (33) that is attached to the alignment rod (31). The alignment key (33) is so located and attached to the alignment rod (31) that the key (33) accurately engages the slot (18) cut through the hollow sleeve (10) of the handle (1) when the first end (34) of the tibial component alignment rod (31) is inserted into the first end (13) of the hollow sleeve (10) of the handle (1). When the tibial component (30) is fitted to the handle (1) in this manner, the alignment key (33) assures that the plane formed by the axis of the alignment rod (31) and pointed end (37) of the locating arm (32) of the tibial component (30) is the same plane as that formed by the axes of the hollow sleeve (10) and pilot tube (12) parts of the handle (1). The alignment key (33) attached to the alignment rod (31) and the corresponding slot (18) cut into the hollow sleeve (10) are one of many possible means for providing the required alignment between the tibial (FIG. 2) or femoral (FIG. 3 or 4) component and the handle (1). This planar alignment is maintained while allowing the tibial component (FIG. 2) to be moved with respect to the handle (1) along the axis of the hollow sleeve (10).

In use (FIG. 5), the sharp pointed second end (37) of the tibial component locating arm (32) is inserted from the posterior into the center of the anatomic attachment of the anterior cruciate ligament on the tibial plateau. Pressure is applied to the locating arm point (37) to prevent it from slipping. Ensuring that any interferring tissue is held out of the way, the inner curved edge (38) of the locating arm (32) is placed securely against the posterolateral corner of the intercondylar notch (70) while maintaining the sharp pointed second end (37) of the locating arm (32) as previously described. The first end (13) of the hollow sleeve (10) of the handle (1) is slid onto the first end (34) of the alignment rod (31) of the tibial component (30). When the knee is set at an angle of about 20 to 30 degrees, the axis of the pilot tube (12) will be correctly aligned with the intended tibial through-hole axis. Tightening of the threaded nut (2) will bring the bone-engaging tooth (19) of the pilot tube (12) into secure contact with the tibia at the correct location and angle and will secure the tip (37) of the tibial component (30) to the pre-selected site on the tibial plateau. With the appropriate hollow bullet-shaped pilot (3) fitted to the pilot tube (12) if necessary, the tibial through-hole (71) or its pilot hole may be drilled at this time.

The femoral component (FIG. 3 or 4) of the drill guide is intended to enable the femoral through-hole (75, 76) to be accurately located and aligned relative to the previously drilled tibial through-hole (71). The femoral component for over-the-top placement (FIG. 3, ref. 40) of a tissue repair device comprises a locating rod (41) and an alignment rod (42) having an alignment key (43). The alignment rod (42) is the same as that for the tibial component (30) except that the length may be different. The alignment key (43) here serves the same function as the alignment key (33) for the tibial component (30).

The femoral component locating rod (41) is required to be of the same diameter as the final drill used to make the tibial through-hole (71). If it is desired to use the drill guide of this invention for drilling through-holes of different diameters, then the locating rod (41) should be made of diameter equal to the smallest through-hole diameter desired. Tubular sleeves can then be provided to increase the diameter of the locating rod (41) for use with through-holes of larger diameters.

The first end (46) of the locating rod (41) is attached to the second end (45) of the alignment rod (42) by any means providing a rigid attachment. Welding an interconnecting plate (48) between them is a preferred method. Alternatively, the locating rod (41) may simply be an extension of the alignment rod (42), a bent or formed angle separating the two. Regardless of attaching means, the angle between the locating rod (41) and the alignment rod (42) should be preferably between about 50 and 60 degrees and most preferably about 55 degrees. A tubular collar (49) with means for slidably attaching may be used on the locating rod (41). The second end (47) of the locating rod (41) is cut off at an angle so that the second end (47) of the locating rod (41) is of elliptical shape. The plane of the elliptical end is perpendicular to the axis of the alignment rod (42).

In use for over-the-top placement (FIG. 6), the femoral component locating rod (41) is inserted through the tibial through-hole (71) until its angle cut second end (47) emerges from the posterolateral corner of the intercondylar notch (70) and the posterior capsule. Longitudinal location of the locating rod (41) is determined by palpation; when the plane of the angle cut end of the locating rod (41) has fully emerged through the posterior capsule and is palpable, the rod (41) is correctly located. The tubular collar (49) on the locating rod (41) is then moved up against the tibia at the anterior end (72) of the tibial through-hole. A thumb-screw (50) secures the collar (49) to the locating rod (41), providing positive longitudinal location of the entire drill guide with respect to the femur and tibia. With the locating rod (41) run through the tibial through-hole (71) and across the posterolateral corner of the intercondylar notch (70) and out the posterior capsule, the femur (73) is properly located with respect to the tibia (74) prior to drilling the femoral through-hole (75). The hollow sleeve (10) of the handle (1) is placed over the threaded first end (44) of the femoral component alignment rod (42) and the nut (2) started on the threads. The angle of the femur with respect to the tibia must be adjusted to about 20 to 30 degrees. Tightening the nut (2) brings the bone engaging tooth (19) of the pilot tube (12) into accurate and positive contact with the femur (73). Using the appropriate hollow bullet-shaped pilot (3) with the pilot tube (12) if required, the pilot hole, if needed, and final femoral through-hole are accurately located and drilled.

The femoral component for anatomic placement (FIG. 4, ref. 51) differs only in detail from the femoral component for over-the-top placement (FIG. 3, ref. 40), the differences being in the included angle between the alignment rod (52) and the locating rod (53), and in the configuration of the second end (58) of the locating rod (53).

For the femoral component for anatomic placement (51), the angle between the alignment rod (52) and locating rod (53) should be between about 40 and 50 degrees and preferably about 45 degrees. The second end (58) of the locating rod (53) has a relieved area (59) with a flat surface parallel to the axis of the locating rod (53) for a distance of about 4 cm., the new surface being perpendicular to the plane through the axes of the alignment rod (52) and the locating rod (53). The relieved area (59) is on the side of the locating rod (53) adjacent to the alignment rod (52) and is preferably cut to the axis of the locating rod (53) and most preferably cut beyond the axis of the locating rod (53) so that, in cross-section, more material has been removed than remains. A pin (60) is inserted into the relieved area (59), the axis of the pin being aligned with the axis of the pilot tube (12) when the handle (1) is placed over the alignment rod (52). The exposed tip of this pin (61) is tapered to a point. The length of this pin (60) is such that the tip of the pin (61) is below the surface of the rod that had been previously milled away, thus still allowing the locating rod (53) to be inserted into the tibial through-hole (71) without interference.

In use (FIG. 7), the locating rod (53) of the femoral component for anatomic placement (51) is inserted into the tibial through-hole (71) until the pin (60) on the second end of the locating rod (53) meets the posterolateral corner of the intercondylar notch (70). The tibia (74) should then be bent with respect to the femur (73) until the posterior outlet of the intercondylar notch contacts the extreme second end (62) of the locating rod (53), the rod lying adjacent to the posteromedial side of the lateral condyle at this time. Also, visual inspection should confirm that the tip of the pin (61) is directed at the desired point of the origin of the anterior cruciate ligament. This included angle between the femur (73) and tibia (74), about 40 to 50 degrees, is correct for locating and drilling the femoral through-hole (76) with respect to the tibial through-hole (71). If a slideably attached cylindrical stop (49) is used on the locating rod (53), it can at this time be slid up the locating rod (53) until it stops against the tibia, the thumb-screw (50) then being used to secure the cylindrical stop (49) to the locating rod (53). This ensures the correct longitudinal placement of the locating rod (53) for drilling the anatomic femoral through-hole. The handle (1) of the drill guide can now be attached to the femoral component (51) and secured to the femur by placing and tightening the nut (2) on the threaded first end (55) of the alignment rod (52).

The drill guide of this invention is novel in several regards. The first is the positive and accurate location provided by the use of threads and a nut to securely engage a tooth of the pilot tube against the surface of the bone, the threads and the nut being located on an axis parallel to but away from the axis of the pilot tube. In this manner the nut and threads are kept away from the surgical site.

The second novel feature is the location of the tibial throughhole by the following three points: (1) The point of the tibial component locating arm centered on the anatomic attachment of the anterior cruciate ligament on the tibial plateau, (2) the point of contact where the curved inner edge of the tibial component locating arm and the posterolateral corner of the intercondylar notch come together, and (3) the center of the toothed end of the pilot tube, this located by forcing the tooth of the pilot tube into the surface of the tibia by tightening the nut. This results in locating the tibial through-hole in such direction that its axis projects between the femoral condyles where the intended prosthesis should be for either the over-the-top or anatomic placement.

A third novel feature of this invention is that the femoral through-hole is located by referencing from the tibial through-hole in a positive and precise manner by the insertion of the femoral component locating rod into the tibial through-hole until it emerges from the posterolateral corner of the intercondylar notch and the posterior capsule. This provides positive and accurate location of the femur with respect to the tibia during drilling of the femoral through-hole. A fourth novel feature is that the positive location of the pilot tube against the distal femur during drilling is ensured by tightening the nut in the same fashion as done previously for the tibial through-hole. Another novel feature of this drill guide is rigidity that is ensured by relatively large diameter parts and by narrow clearances between slideably attached parts. Still another novel feature is that the angular relationship between the tibial and femoral through-holes is consistently provided by the fixed angle between the alignment rod and the locating rod of the femoral component. Additionally, this device is capable of accurately locating a femoral through-hole for use with a tissue repair device placed in either over-the-top or anatomical position.

Further novel features of the drill guide device of the present invention include the following:

1. The axis of the tibial through-hole is on the same axis as the intra-articular portion of the replacement ligament when the knee is near full extension and the replacement ligament is consequently under maximum stress;

2. The axes of the tibial through-hole and femoral through-hole are in the same plane when the knee is near full extension and the replacement ligament is under maximum stress; and 3. The posterior exit site of the femoral through-hole will be in the optimal position for over-the-top ligament routing across the posterolateral aspect of the intercondylar notch.

While this drill guide device is intended primarily for use in the implantation of anterior cruciate ligament repair devices, its rigidity and ability to be conveniently and securely attached to bone prior to drilling enable it to be used for other applications.

We claim:

1. An orthopedic drill guide device comprising:
   (a) a handle;
   (b) a tibial component; and
   (c) a threaded nut for securing the tibial component to the handle;
   said handle having an arm with a first and second end, attached to said first end of said arm is a hollow sleeve having a longitudinal axis and a means for slideably receiving and aligning with the tibial component, attached to said second end of said arm is a pilot tube with a longitudinal axis parallel to the longitudinal axis of said hollow sleeve, said pilot tube having at one end at least one bone-engaging tooth;
   said tibial component having an alignment rod with a first and second end, said alignment rod having a threaded section extending over all or part of its length beginning from said first end, said alignment rod having a longitudinal axis and engaging said slideably and receiving aligning means of the hollow sleeve of the handle in a direction parallel to the longitudinal axis of the alignment rod, said tibial component having a locating arm with a first and second end and an inner and outer edge, the first end of said locating arm being attached to the second end of said alignment rod, the second end of said locating arm being tapered to a sharp point, the inner edge of said locating arm intended to contact the posterolateral corner of the intercondylar notch of a femur bone, said inner edge contact in conjunction with the tapered point of the second end of the locating arm and a tooth of the pilot tube of the handle planarly locating said drill guide for the purpose of drilling a through-hole in a bone;

wherein the threaded section of the tibial component alignment rod is positioned in the hollow sleeve of the handle so that the means for slideably receiving and aligning the alignment rod with the hollow sleeve is engaged, the sharp pointed second end of the tibial component locating arm is positioned to engage one surface of a tibial bone and the bone engaging tooth of the tubular pilot of the handle is positioned to engage a second surface of the tibial bone, the nut being threaded onto the alignment rod threads to compressively secure the handle and tibial component to the bone for the purpose of aligning and drilling a through-hole in said tibial bone.

2. The drill guide device of claim 1 in which a hollow bullet-shaped pilot of smaller inside diameter than the pilot tube of the handle is present in the pilot tube.

3. The drill guide device of claim 2 in which said hollow bullet-shaped pilot incorporates a retaining ring that removably retains said hollow bullet-shaped pilot in the pilot tube of the handle.

4. The drill guide device of claim 1 in which said means for slideably receiving and aligning comprises the hollow sleeve of the handle and alignment rod of the tibial component having mating cross sections, said cross sections being of other than round form.

5. The drill guide device of claim 4 in which said cross sections are of square form.

6. The drill guide device of claim 1 in which said means for slideably receiving and aligning comprises a longitudinal slot cut through the wall of the hollow sleeve of the handle parallel to the axis of the hollow sleeve, and a pin protruding from the surface of the alignment rod of the tibial component, said pin intended to slideably receive and align with the slot of said hollow sleeve.

7. The drill guide device of claim 1 in which said means for slideably receiving and aligning comprises a longitudinal slot cut through the wall of the hollow sleeve of the handle parallel to the axis of the hollow sleeve, and a key protruding from the surface of the alignment rod of the tibial component, said key intended to slideably receive and align with the slot of said hollow sleeve.

8. An orthopedic drill guide device comprising:
(a) a handle;
(b) a femoral component; and
(c) a threaded nut for securing the femoral component to the handle;
said handle having an arm with a first and second end, attached to said first end of said arm is a hollow sleeve having a longitudinal axis and a means for slideably receiving and aligning with the femoral component, attached to said second end of said arm is a pilot tube with a longitudinal axis parallel to the longitudinal axis of said hollow sleeve, said pilot tube having at one end at least one bone-engaging tooth;
said femoral component having an alignment rod with a first and second end, said alignment rod having a threaded section extending over all or part of its length beginning from said first end, said alignment rod having a longitudinal axis and engaging said means for slideably receiving and aligning of the hollow sleeve of the handle in a direction parallel to the longitudinal axis of the alignment rod, said femoral component having a locating rod with a first and second end, the first end of said locating rod being attached to the second end of said alignment rod at an included angle between about 40 and 60 degrees;

wherein the locating rod of the femoral component is positioned in a previously drilled through-hole in a tibial bone, the hollow sleeve of the handle is positioned over the alignment rod of the femoral component so that the means for slideably receiving and aligning the alignment rod with the hollow sleeve is engaged and the bone engaging tooth of the tubular pilot of the handle is positioned to engage a surface of a femur, the nut being threaded onto the alignment rod threads to compressively secure the handle and femoral component to the femur and tibia bones for the purpose of aligning and drilling a through-hole in the femur bone.

9. The drill guide device of claim 8 in which the locating rod of the femoral component is increased in diameter by fitting a tubular sleeve over the curved outer surface of said locating rod.

10. The drill guide device of claim 8 in which the femoral component is intended for use in locating a tissue repair device for over-the-top placement, the second end of the locating rod of said femoral component having a surface perpendicular to the axis of the alignment rod.

11. The drill guide device of claim 10 in which the included angle between the alignment rod and the locating rod of the femoral component is between about 50 and 60 degrees.

12. The drill guide device of claim 10 in which the included angle between the alignment rod and the locating rod of the femoral component is about 55 degrees.

13. The drill guide device of claim 8 in which the femoral component is intended for use in locating a tissue repair device for anatomical placement, the second end of the locating rod of said femoral component being cut away so as to provide a relieved area with a flattened surface, said surface being perpendicular to the plane through the axes of the alignment rod and locating rod, said relieved area being on the side of the locating rod adjacent to the alignment rod, said relieved area incorporating a pin lying along the axis of the pilot tube, said pin having an exposed pointed tip, said pin being of length such that the locating rod may be inserted without interference into a tibial through-hole of diameter slightly larger than the first end of the locating rod, said locating rod being of length such that the second end of said locating rod serves as a stop against the posterior outlet of the femur when the included angle between the femur and tibia are correct for drilling the femoral through-hole in proper relationship to the tibial through-hole.

14. The drill guide device of claim 13 in which the included angle between the alignment rod and the locating rod of the femoral component is between about 40 and 50 degrees.

15. The drill guide device of claim 13 in which the included angle between the alignment rod and the locating rod of the femoral component is about 45 degrees.

16. The drill guide device of claim 8 in which a hollow bullet-shaped pilot of smaller inside diameter than the pilot tube of the handle is present in the pilot tube.

17. The drill guide device of claim 16 in which said hollow bullet-shaped pilot incorporates a retaining ring that removably retains said hollow bullet-shaped pilot in the pilot tube of the handle.

18. The drill guide device of claim 8 in which said means for slideably receiving and aligning comprises the hollow sleeve of the handle and alignment rod of the femoral component having mating cross sections, said cross sections being of other than round form.

19. The drill guide device of claim 18 in which said cross sections are of square form.

20. The drill guide device of claim 8 in which said means for slideably receiving and aligning comprises a longitudinal slot cut through the wall of the hollow sleeve of the handle parallel to the axis of the hollow sleeve, and a pin protruding from the surface of the alignment rod of the femoral component, said pin intended to slideably receive and align with the slot of said hollow sleeve.

21. The drill guide device of claim 8 in which said means for slideably receiving and aligning comprises a longitudinal slot cut through the wall of the hollow sleeve of the handle parallel to the axis of the hollow sleeve, and a key protruding from the surface of the alignment rod of the femoral component, said key intended to slideably receive and align with the slot of said hollow sleeve.

22. The drill guide device of claim 1 or 8 in which said means for slideably receiving and aligning comprises mating splines cut into the interior surface of the hollow sleeve of said handle and the exterior unthreaded surface of said alignment rod, said splines oriented parallel to the axes of said hollow sleeve and alignment rod.

23. The drill guide device of claim 8 having a cylindrical stop slideably attached to the locating rod of said femoral component.

* * * * *